United States Patent
Walton, III (10) Patent No.: US 9,348,970 B2
(45) Date of Patent: *May 24, 2016

(54) SYSTEM AND METHOD FOR PROVIDING ACCESS TO ELECTRONICALLY STORED MEDICAL INFORMATION

(71) Applicant: James F. Walton, III, Tallahassee, FL (US)

(72) Inventor: James F. Walton, III, Tallahassee, FL (US)

(*) Notice: Subject to any disclaimer, the term of this patent is extended or adjusted under 35 U.S.C. 154(b) by 51 days.

This patent is subject to a terminal disclaimer.

(21) Appl. No.: 14/665,701

(22) Filed: Mar. 23, 2015

(65) Prior Publication Data

US 2016/0042125 A1    Feb. 11, 2016

Related U.S. Application Data

(62) Division of application No. 14/454,799, filed on Aug. 8, 2014, now Pat. No. 9,111,167.

(51) Int. Cl.
*G06K 19/06* (2006.01)
*G06F 19/00* (2011.01)
*G06K 1/18* (2006.01)

(52) U.S. Cl.
CPC ............ *G06F 19/322* (2013.01); *G06F 19/323* (2013.01); *G06K 1/18* (2013.01)

(58) Field of Classification Search
CPC ......................... G06F 19/322; G06K 19/06037
USPC .......................................................... 235/487
See application file for complete search history.

(56) References Cited

U.S. PATENT DOCUMENTS

| | | | |
|---|---|---|---|
| 5,658,016 | A | 8/1997 | Goeken |
| D426,833 | S | 6/2000 | Vaneill |
| 6,513,720 | B1 | 2/2003 | Armstrong |
| 6,747,561 | B1 | 6/2004 | Reeves |
| 6,751,805 | B1 | 6/2004 | Austion |
| 6,845,063 | B2 | 1/2005 | Mitchell |
| 7,827,043 | B2 | 11/2010 | Tahan |
| 8,960,555 | B1 * | 2/2015 | Walton, III ................... 235/487 |
| 2002/0120470 | A1 | 8/2002 | Trice, Sr. |
| 2003/0058110 | A1 | 3/2003 | Rich |
| 2003/0101077 | A1 | 5/2003 | Wohl |
| 2003/0150143 | A1 | 8/2003 | Hazard |
| 2005/0194270 | A1 | 9/2005 | Gombar |
| 2006/0010012 | A1 | 1/2006 | Franzblau et al. |
| 2006/0015368 | A1 | 1/2006 | Hockey |
| 2006/0086226 | A1 | 4/2006 | Kamber |
| 2006/0142057 | A1 | 6/2006 | Schuler et al. |
| 2007/0158411 | A1 | 7/2007 | Krieg, Jr. |
| 2007/0265884 | A1 | 11/2007 | Lubell et al. |
| 2008/0126729 | A1 | 5/2008 | Cai et al. |
| 2008/0319798 | A1 | 12/2008 | Kelley |

(Continued)

*Primary Examiner* — Christle I Marshall
(74) *Attorney, Agent, or Firm* — Livingston Loeffler, P.A.; Edward M. Livingston, Esq.; Bryan L. Loeffler, Esq.

(57) ABSTRACT

A method and system for storing medical information of an individual with a service provider and providing access to that medical information to first responders and medical personnel remotely. An individual's medical information may be accessed by first responders after being authenticated by the service provider. Access to the medical information is monitored to prevent unauthorized access and to store time and location when medical information is accessed by a first responder. The medical information may be accessed by a mobile software application that allows the first responder to scan a machine-readable medium linked to the individual's medical information stored by the service provider.

22 Claims, 5 Drawing Sheets

(56) References Cited

U.S. PATENT DOCUMENTS

| | | |
|---|---|---|
| 2009/0076849 A1 | 3/2009 | Diller |
| 2009/0101721 A1 | 4/2009 | Hawthorne et al. |
| 2009/0295569 A1 | 12/2009 | Corwin et al. |
| 2010/0115609 A1 | 5/2010 | Spence |

* cited by examiner

SYSTEM AND METHOD FOR PROVIDING ACCESS TO ELECTRONICALLY STORED MEDICAL INFORMATION

CROSS-REFERENCE TO RELATED APPLICATIONS

This application is a divisional application of U.S. patent application Ser. No. 14/454,799 filed on Aug. 8, 2014 which is currently pending. The patent application identified above is incorporated herein by reference in its entirety to provide continuity of disclosure.

FIELD OF THE INVENTION

This invention relates to providing personal medical information to first responders and other medical personnel through the use of machine-readable mediums, electronic devices and the Internet.

BACKGROUND OF THE INVENTION

During a medical emergency, time is of the essence for a patient to receive the proper care from first responders. In such instances it is important that first responders are aware of a patient's medical history including allergies to drugs, current medications and medical conditions. It also becomes necessary to have the patient's emergency contact information and physician contact information. In many instances patients are unconscious and unable to provide any information to first responders. Conventional methods of providing such information include medical identification bracelets which may list an individual's allergies or medical conditions. Another solution to this is storing medical information electronically so first responders and medical personnel can access the information on an electronic device.

A problem arises with maintaining the security and privacy of sensitive medical information stored remotely and/or on electronic mediums. It is important to only allow access to such sensitive information to individuals who have been confirmed as a first responder and/or other medical personnel and, thus, authorized to access an individual's medical records.

Therefore, the need exists for a system and method of providing access to electronically stored medical information that allows an authenticated first responder or medical personnel to access an individual's medical information remotely and securely via an electronic device.

SUMMARY OF THE INVENTION

The primary object of the present invention is to provide a system and method of providing access to electronically stored medical information that allows a user to easily store personal and medical information in a central database.

An additional object of the present invention is to provide a system and method of providing access to electronically stored medical information that is easily identifiable by a first responder as being a medical information device.

An additional object of the present invention is to provide a system and method of providing access to electronically stored medical information that provides a medical worker remote access to an individual's medical information.

An additional object of the present invention is to provide a system and method of providing access to electronically stored medical information that only allows access to such sensitive information to properly authenticated and authorized first responders and other medical personnel.

The present invention fulfills the above and other objects by providing a system and method of providing access to electronically stored medical information, such as blood type, allergies, medical conditions, present medications, age, doctor information and emergency contact information. The medical information may be accessed directly from a machine-readable medium and/or from a remote database over the Internet wherein the medical information stored in the remote database is linked to a specific machine-readable medium and/or identification number. This is accomplished by using a one-dimensional, two dimensional or three dimensional barcode, such as a Quick Response Code ("QR code") or other matrix barcode that is capable of storing text and/or URL information that may be opened by an electronic device or other imaging device, such as a smart phone. The barcode may be printed directly on an identification card or on a bracelet, key chain, identification card, driver's license, insurance card and/or on an adhesive-backed material and then adhered to an existing card, such as a driver's license or other identification card. Alternatively, the barcode or other machine-readable medium may be printed on a sleeve into which an identification card, such as a driver's license, is placed.

An additional advantage of the method and system of the present invention is an added layer of security for allowing access to stored medical records and information by requiring first responders and other medical personnel to register with the service provider and be pre-authorized by having their credentials authenticated. After the first responder or other medical personnel has been confirmed and pre-authorized they are allowed to use a downloadable software application from the service provider to access medical records for specific individuals. The first responder or other medical personnel must enter a security code or perform some other security recognition function, such as biometric recognition prior to accessing medical records. This ensures that only preauthorized first responder or other medical personnel are able to access an individual's medical information. This also allows the service provider to track who is accessing an individual's medical information, when the information is accessed and the geographic location of the request.

The software will be used in retrieving medical emergency information for anyone involved in an emergency situation. The software will be available preferably as a free download, and can be used by EMTs, medical personnel, hospitals, home health care providers and so forth as well as the individual owner of a medical information account or his or her appointed representatives (collectively referred to herein as "first responders" and/or "medical personnel"). First responders and medical personnel will be verified by a registration process with the service provider that requires them to provide their license number and/or other relevant identifying data. Once verified, the first responder will be able to access an individual's emergency medical information. At the time of administering aide, the first responder can access electronic emergency medical records by: (1) Scanning 1-dimensional, 2-dimensional or 3-dimensional barcodes commonly used on driver's licenses, social services cards, national identification cards, and patient care provider cards; and/or (2) manually inputting identifying information into an electronic device, such as a driver's license number, social services card number, national identification card number, or other patient care provider number. The identifying information may be input into the electronic device using a keyboard, voice recognition, a blue-tooth device, touch screen, radio frequency identification ("RFID"), near field communications ("NFC"), biometrics, eye movement, facial recognition, head or body gestures. The emergency medical records will then be delivered to the first responder and will contain one or more of the following: user profile data (photo, first name, middle name, last name, birthday, gender, blood type, race, primary language, secondary language, address, city, state, zip, height, weight, hair color, eye color, cell phone number, home phone number, work phone number, fax number, phone number, email address, insurance company name, group number, policy number, insurance phone number, organ donor (Yes or No), allow blood transfusions (yes or no), emergency contacts (first name, last name, address, city, state, zip code, cell phone number, work phone number, home phone number, email address, relationship), medications (name, dosage, how often), medical conditions (asthma, COPD, seizure disorder, dementia, Alzheimer's, hyperglycemia, hypoglycemia, diabetes type 1, diabetes type 2, high blood pressure, contact lenses, rheumatic fever, pacemaker, heart stent, fistula and so forth), allergies (name, description, notes/info), physician information (name, address, city, state, zip code, phone number, email address, specialty). The first responder or medical personnel requesting the medical information is then documented with regard to his or her name, date and time of access, and GPS location when the information is requested.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which.

DESCRIPTION OF THE PREFERRED EMBODIMENTS

Figure 1:
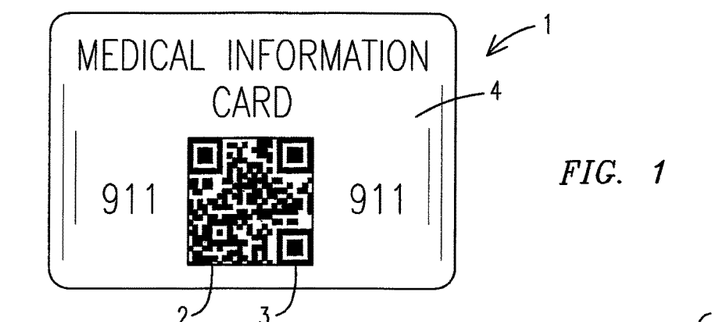
FIG. 1 is a front view of an identification card being used as a medical information device of the present invention.

With reference to FIG. 1, a front view of an identification card 4 being used as a medical information device 1 of the present invention is illustrated. The medical information device 1 allows an individual to store emergency medical information, such as blood type, allergies, medical conditions, present medications, age, doctor information and emergency contact information and to provide a means for retrieving that information to a first responder or other medical personnel. First responders or medical personnel may include certified EMTs, doctors, nurses, dentists, fire fighters, law enforcement, hospital staff, emergency room staff, ambulance staff, home health care providers, family members, next of kin, friends, coaches, school nurses, team physicians and so forth. The medical information device 1 is capable of storing medical information directly therein and/or of providing remote access to medical information stored in a central database. This is accomplished by using a machine-readable medium, such as a barcode 2, a Quick Response Code ("QR code") 3 or other matrix barcode, that is capable of storing text and/or URL information that may be opened by an electronic device or other imaging device, such as a smart phone. The barcode 2 may be printed directly on a medical information device 1, such as an identification card 4 (as illustrated here), a bracelet, a keychain, sleeve for an identification card and so forth.

Figure 2:
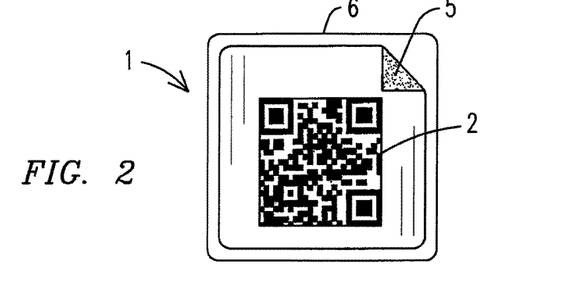
FIG. 2 is a front view of a barcode of the present invention printed on an adhesive-backed material.

With reference to FIG. 2, a front view of a barcode 2 of the present invention printed on an adhesive-backed material 5 is illustrated. The barcode 2 is a machine-readable medium that may have medical information directly stored therein and/or provide a URL for remote access of medical information stored in a central database. The barcode 2 illustrated here may be used by peeling off a backing 6 and adhering the adhesive backed material 5, such as paper, plastic, foil and so forth, to any object, such as an identification card, bracelet, keychain and so forth, sleeve for an identification card thereby making the object a medical information device 1.

Figure 3A:
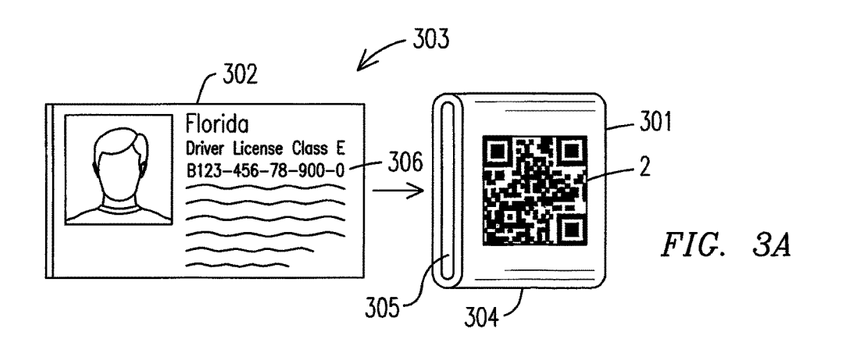
FIG. 3A is an exploded front perspective view of a sleeve for an identification card being used as a medical information device of the present invention.
Figure 3B:
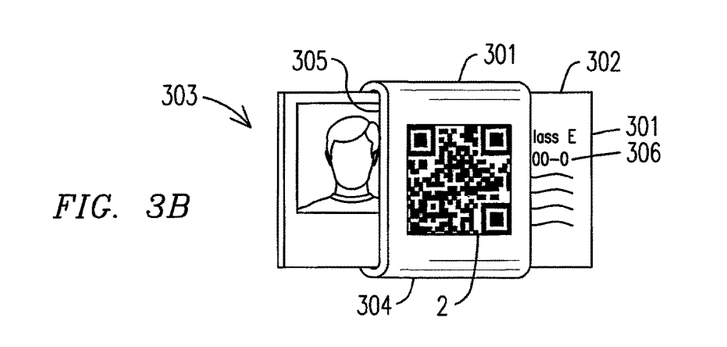
FIG. 3B is a front perspective view of a sleeve for an identification card being used as a medical information device of the present invention.

With reference to FIGS. 3A and 3B, an exploded front perspective view and a front perspective view, respectively, of a sleeve 301 for an identification card 302 being used as a medical information device 303 of the present invention are illustrated. The sleeve 301 comprises a perimeter wall 304 having at least one opening 305 to allow the identification card 302 to be inserted into the sleeve 301. A barcode 2 or other machine-readable medium electronic medium may be printed directly on the sleeve 301 or adhered to the sleeve 301 like a sticker. A new or pre-existing identification number 306, such as a driver's license number, insurance number and so forth, may be linked to an individual's account with the service provider so that it may be entered manually by a first responder to access the individual's medical records.

Figure 4:
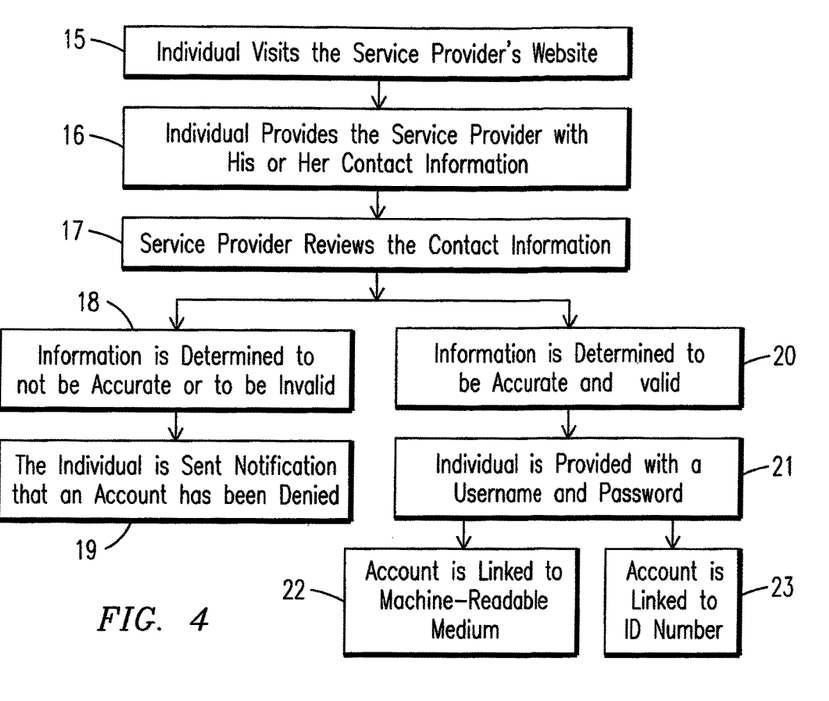
FIG. 4 is a flow chart showing an individual signing up for an account with a service provider that provides a medical information device to the individual.

With reference to FIG. 4, a flow chart showing an individual signing up for an account with a service provider that provides a medical information device to the individual is illustrated. First, the individual visits the service provider's website 15. Then, the individual provides the service provider with his or her contact information, which includes the individual's name, address, phone number, email address and so forth 16. The service provider then reviews the contact information to determine the accuracy of the information and the validity of the information 17. If the information is determined to not be accurate or to be invalid 18, then the individual is sent notification, preferably via email, that an account has been denied 19. If the information is determined to be accurate and valid 20, then the individual is sent an approval, preferably via email, that an account has been created and the individual is provided with a username and password 21. Next, the individual's account is liked to a machine-readable medium, such as a bar code, QR code, RFID, thumb drive, magnetic strip and so forth, 22 and/or to an identification number, such as a driver's license number, insurance number and so forth 23.

Figure 5:
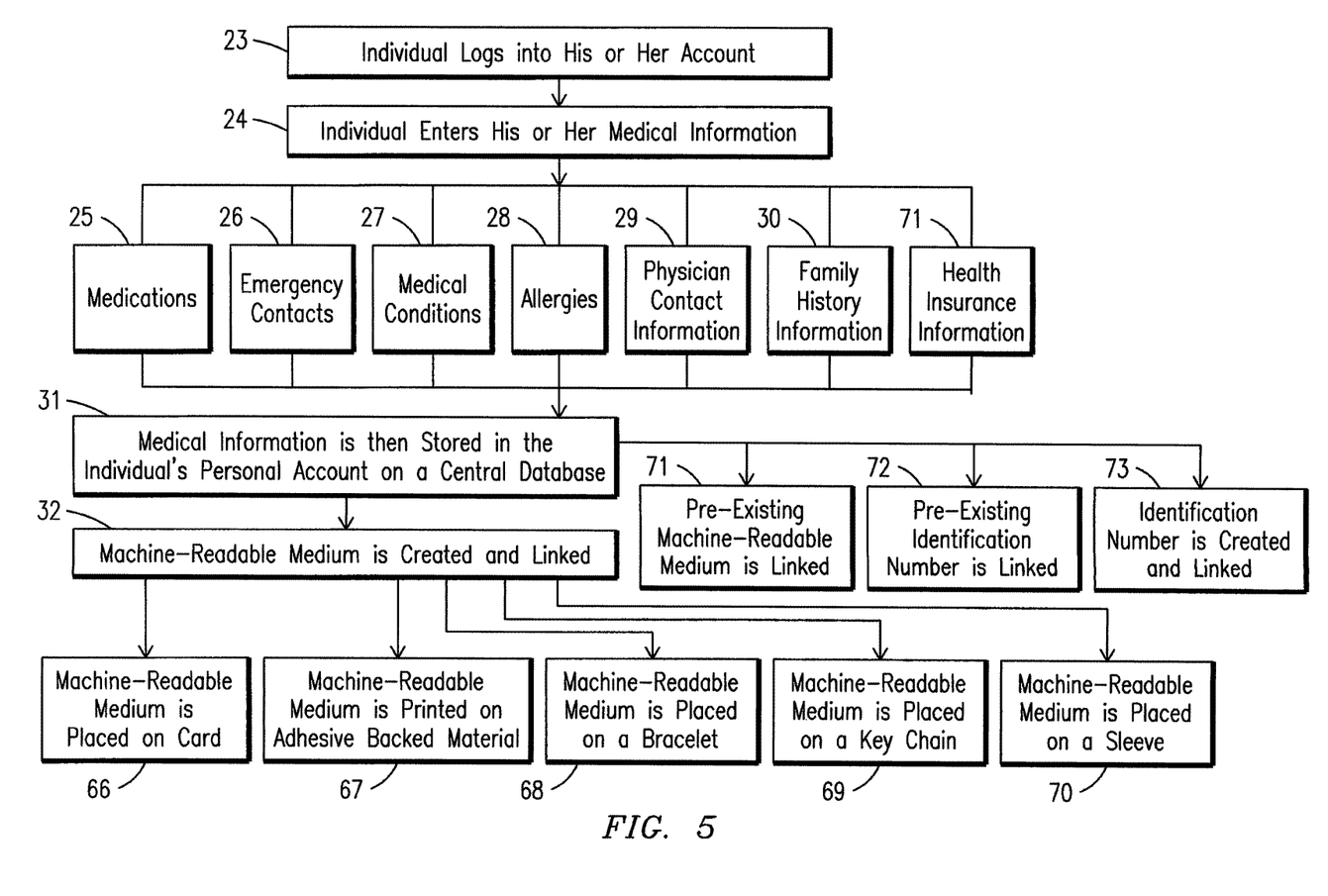
FIG. 5 is a flow chart showing the system and method of the present invention in which an individual enters medical information into an online account.

With reference to FIG. 5, a flow chart showing the system and method of the present invention in which an individual enters medical information into an online account is illustrated. First, the individual logs into his or her account using the username and password provided by the service provider 23. Then, the individual enters his or her medical information 24, which includes medications 25, emergency contacts 26, medical conditions 27, allergies 28, physician contact information 29, family history information 30, health insurance information 71 and so forth. The medical information is then stored in the individual's personal account in a central database 31. A bar code is then created that is personalized to the individual's account and has text medical information and/or a URL that directs a user to the individual's medical information remotely after the bar code is scanned 32. The bar code may be printed on an identification card 66, an adhesive backed material 67, a bracelet 68, a keychain 69, and/or a sleeve 70.

Figure 6:
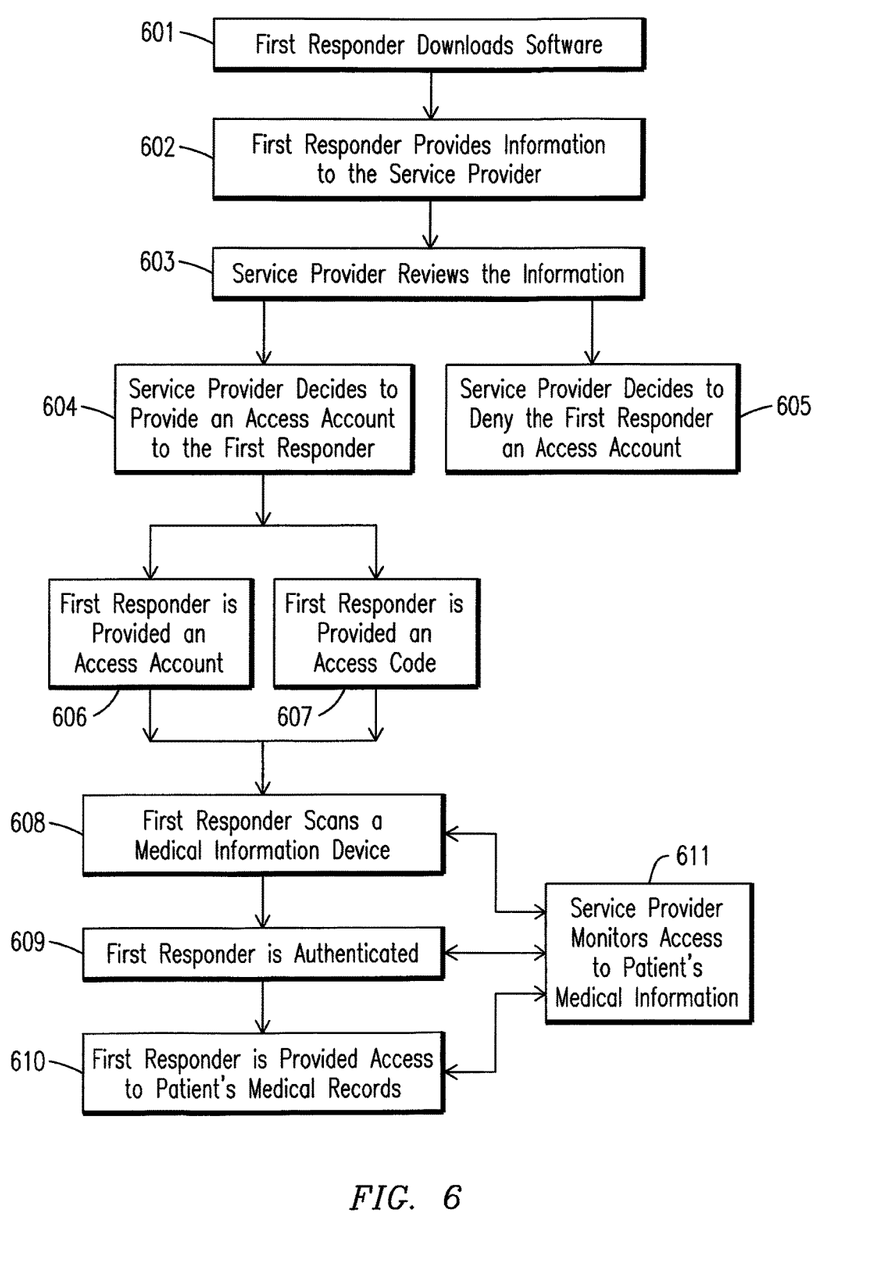
FIG. 6 is a flowchart showing the system and method of the present invention in which a first responder (or other medical personnel) is provided an account with the service provider to allow the first responder to read medical information stored on a patient's medical information device and/or to access information remotely from the central database.

With reference to FIG. 6, a flowchart showing the system and method of the present invention in which a first responder (or other medical personnel) is provided an account with the service provider to allow the first responder to read medical information stored on a patient's medical information device and/or to access information remotely from the central database is illustrated. First, the first responder downloads a software application from the service provider 601. Said software application may be downloaded directly from the service provider or from any app store online over the Internet. Next, the first responder registers his or her account by providing information, such as name, address, employer, position and so forth, to the service provider 602. The first responder may also be required to provide government issued identification numbers confirming the first responder's certifications and/or employment with a medical provider. Then, the service provider reviews the information and determines if the information is correct and accurate 603. Next, the service provider decides to provide an access account to the first responder 604 or denies the first responder an access account 605. If the service provider decides to provide an access account to the first responder 604, then the first responder is provided an access account 606 and provided an access code 607 to allow the first responder to read medical information stored on a patient's medical information device and/or to access information remotely from the central database through the service provider's website and/or through the downloaded mobile application software. When the first responder scans an electronic storage means on a medical information device with an electronic device (such as a smart phone) using the downloaded software 608, the first responder is required to enter the access code or to be authenticated by other means, such as biometric scans, 609 prior to obtaining access to any medical information stored directly on the medical information device and/or accessing information remotely from the central database 610. The service provider is then able to ensure that medical information is kept private. The service provider is then able to monitor who is accessing a patient's medical information and when and where the medical information is being accessed 611.

Figure 7:
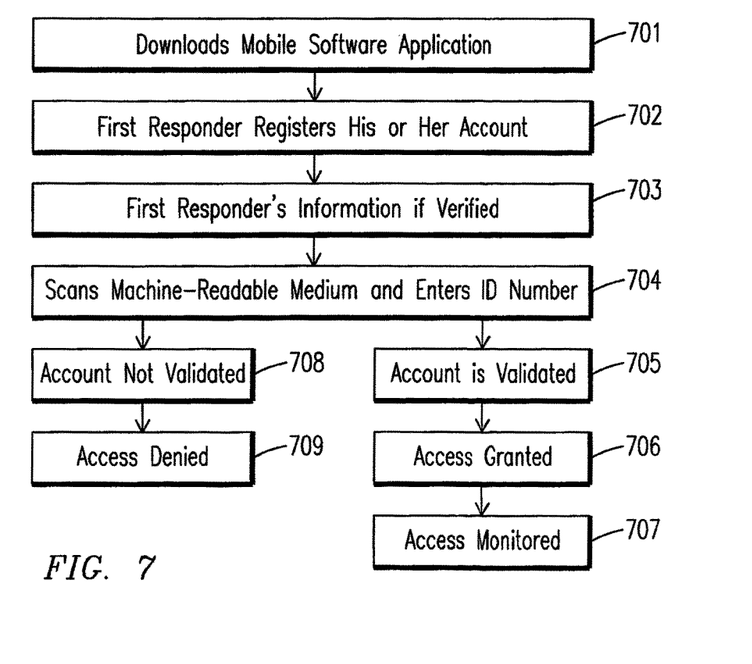
FIG. 7 is a flowchart showing the system and method of the present invention in which a first responder (or other medical personnel) downloads a mobile software application from the service provider and the authentication of the first responder.

With reference to FIG. 7, a flowchart showing the system and method of the present invention in which a first responder (or other medical personnel) downloads a mobile software application from the service provider and the authentication of the first responder is illustrated. First, a first responder (or other medical personnel) downloads a mobile software application to their electronic device from an APP store or directly from the service provider 701. Then, the first responder registers his or her account using a state issued license number or other relevant information 702. Next, the information is verified so the first responder may use the software and/or the service provider's website to access an individual's electronic emergency medical records 703. Then, the first responder scans a bar code or other machine-readable medium or manually inputs an identification number of the individual receiving treatment 704. Next, the first responder's registration with the service provider is validated to ensure it has not expired or become invalid 705. If valid, then the individual's medical records are displayed 706, and the first responder's access is logged 707 with regard to time and date the first responder accessed the record and the geo-location including the longitude/latitude of where the record was accessed. If not valid, an indicator is provided to the first responder that his or her registration is not valid 708 and access is denied.

Figure 8:
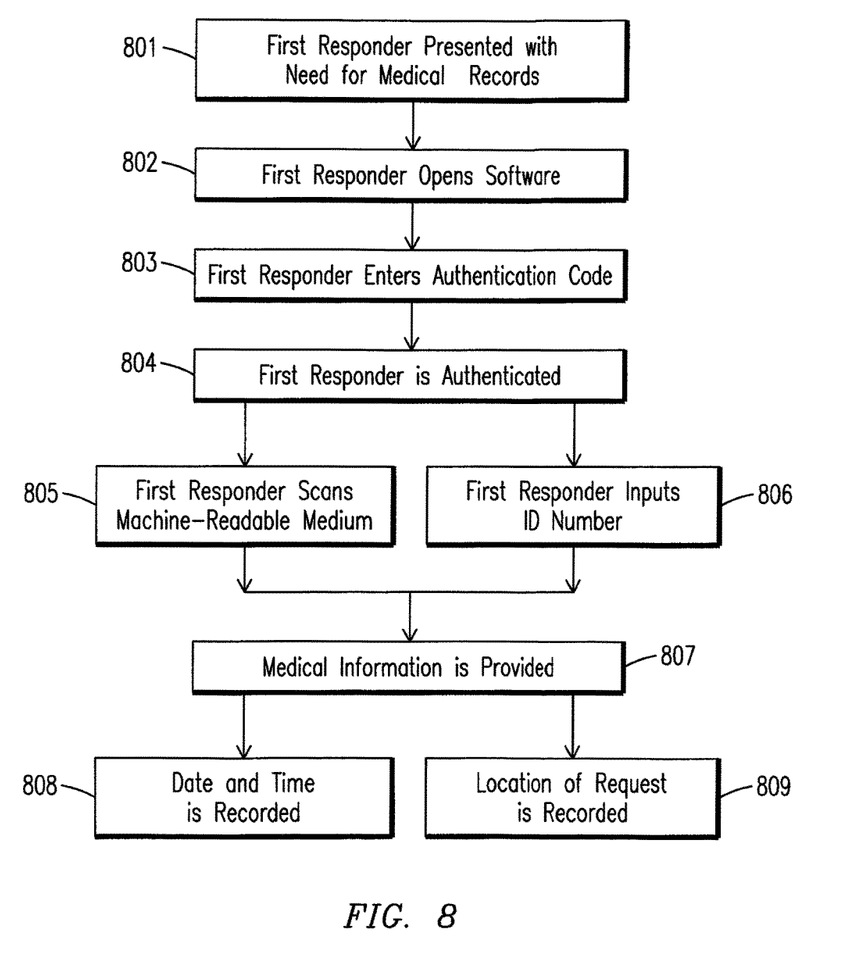
FIG. 8 is a flowchart showing the system and method of the present invention in which a first responder retrieves medical information from a patient's medical information device.

With reference to FIG. 8, a flowchart showing the system and method of the present invention in which a first responder retrieves medical information from a patient's medical information device is illustrated. First, a first responder responds to and/or is presented with a medical emergency or other need to access an individual's medical records 801. Then, the first responder locates the machine-readable medium 802. Next, the first responder opens the service provider's software on his or her electronic device 803. Then, the first responder enters his or her authentication code or other identifying means 804. Next, the first responder scans the machine-readable medium using the electronic device 805 or enters the individual's identification number, such as a driver's license number 806. Then, the medical information is provided to the first responder 807. Next, the time and date of the request is recorded 808, and the location of the request is recorded 809.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Having thus described my invention, I claim:

1. A method for storing medical information of an individual with a service provider and providing access to that medical information to first responders and medical personnel comprising the steps of:
   a. an individual providing the service provider with his or her contact information;
   b. the service provider reviewing the contact information and rendering a decision on whether to allow the individual to have an account;
   c. an individual creating an account with a service provider over the internet;
   d. the individual's medical information being provided to the service provider to be saved in a central database;
   e. the service provider authenticating a first responder;
   f. the first responder being provided an account with the service provider; and
   g. the service provider providing first responder with remote access to the individual's medical information.

2. The method of claim 1 further comprising steps of:
   the service provider deciding to allow the individual to have an account; and the service provider creating an account and providing the individual with a username and password.

3. The method of claim 1 further comprising a step of:
the service provider linking the individual's account to a machine-readable medium.

4. The method of claim 3 further comprising a step of:
the first responder scanning the machine-readable medium using an electronic device and obtaining the individual's medical information from the service provider.

5. The method of claim 4 further comprising a step of:
the date and time the first responder scanned the machine-readable medium being recorded by the service responder.

6. The method of claim 4 further comprising a step of:
the location of the first responder when the first responder scanned the machine-readable medium being recorded by the service responder.

7. The method of claim 1 further comprising a step of:
the service provider linking the individual's account to an identification number.

8. The method of claim 7 further comprising a step of:
the first responder entering the identification number into an electronic device and obtaining the individual's medical information from the service provider.

9. The method of claim 8 further comprising a step of:
the date and time the first responder uses the individual's identification number to obtain the individual's medical records being recorded by the service responder.

10. The method of claim 8 further comprising a step of:
the location of the first responder when the first responder used the individual's identification number to obtain the individual's medical records being recorded by the service responder.

11. The method of claim 1 further comprising a step of:
the first responder downloading software from the service provider onto an electronic device.

12. A system for storing medical information of an individual with a service provider and providing access to that medical information to first responders and medical personnel comprising:
an individual providing the service provider with his or her contact information;
the service provider reviewing the contact information and rendering a decision on whether to allow the individual to have an account;
an individual creating an account with a service provider over the internet;
the individual's medical information being provided to the service provider to be saved in a central database;
the service provider authenticating a first responder;
the first responder being provided an account with the service provider; and
the service provider providing first responder with remote access to the individual's medical information.

13. The system of claim 12 further comprising:
the service provider deciding to allow the individual to have an account; and
the service provider creating an account and providing the individual with a username and password.

14. The system of claim 12 further comprising:
the service provider linking the individual's account to a machine-readable medium.

15. The system of claim 14 further comprising:
the first responder scanning the machine-readable medium using an electronic device and obtaining the individual's medical information from the service provider.

16. The system of claim 15 further comprising:
the date and time the first responder scanned the machine-readable medium being recorded by the service responder.

17. The system of claim 15 further comprising:
the location of the first responder when the first responder scanned the machine-readable medium being recorded by the service responder.

18. The system of claim 12 further comprising:
the service provider linking the individual's account to an identification number.

19. The system of claim 18 further comprising:
the first responder entering the identification number into an electronic device and obtaining the individual's medical information from the service provider.

20. The system of claim 19 further comprising:
the date and time the first responder uses the individual's identification number to obtain the individual's medical records being recorded by the service responder.

21. The system of claim 19 further comprising:
the location of the first responder when the first responder used the individual's identification number to obtain the individual's medical records being recorded by the service responder.

22. The system of claim 12 further comprising:
the first responder downloading software from the service provider onto an electronic device.

* * * * *